United States Patent [19]

Beckmann et al.

[11] Patent Number: 5,298,635
[45] Date of Patent: Mar. 29, 1994

[54] TERTIARY AMIDES USEFUL AS LOW-FOAM WETTING AGENTS IN THE TEXTILE INDUSTRY

[75] Inventors: Eberhard Beckmann, Neustadt, Fed. Rep. of Germany; Ralf Brueckmann, Charlotte, N.C.; Johannes P. Dix, Weisenheim; Peter Freyberg, Ludwigshafen; Erich Kromm, Weisenheim, all of Fed. Rep. of Germany

[73] Assignee: BASF Aktiengesellschaft, Ludwigshafen, Fed. Rep. of Germany

[21] Appl. No.: 60,969

[22] Filed: May 14, 1993

[30] Foreign Application Priority Data

May 16, 1992 [DE] Fed. Rep. of Germany ....... 4216316

[51] Int. Cl.$^5$ .......................... C11D 3/30; C11C 1/02
[52] U.S. Cl. ......................................... 554/35; 554/61; 8/586; 8/602; 8/609; 252/8.8
[58] Field of Search ............... 554/35, 61; 8/586, 602, 8/609; 252/8.8

[56] References Cited

U.S. PATENT DOCUMENTS

| | | | |
|---|---|---|---|
| 468,198 | 1/1975 | Khan | 260/92.3 |
| 5,124,079 | 6/1992 | Smid et al. | 554/61 X |
| 5,198,559 | 3/1993 | Lahtinen et al. | 554/35 |
| 5,221,757 | 6/1993 | Ohashi et al. | 554/61 X |
| 5,247,121 | 9/1993 | Sebag et al. | 554/35 X |

FOREIGN PATENT DOCUMENTS 2169916  7/1986  United Kingdom .

OTHER PUBLICATIONS

Journal of the American Oil Chemists' Society, vol. 63, No. 12, Dec. 1986, pp. 1579–1583.

*Primary Examiner*—Arthur C. Prescott
*Attorney, Agent, or Firm*—Oblon, Spivak, McClelland, Maier & Neustadt

[57] ABSTRACT

Tertiary amides useful as low-foam wetting agents in the textile industry have the formula I

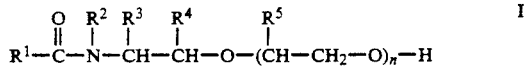

where
$R^1$ is straight-chain or branched $C_5$–$C_{17}$-alkyl or -alkenyl,
$R^2$ is straight-chain or branched $C_3$–$C_6$-alkyl,
$R^3$, $R^4$ and $R^5$ are each independently of the others hydrogen, methyl or ethyl, and
$n$ is from 3 to 15.

7 Claims, No Drawings

TERTIARY AMIDES USEFUL AS LOW-FOAM WETTING AGENTS IN THE TEXTILE INDUSTRY

The present invention relates to the use of tertiary amides as low-foam wetting agents in the textile industry.

Since some of these tertiary amides are novel compounds, the invention also relates to these novel compounds.

In textile dyeing, wetting agents are required in the preparatory process, in the pretreatment and in the dyeing itself. Wetting has the purpose of conferring on the textile material the absorbency that is required for all subsequent wet processing operations.

J. Am. Oil Chem. Soc. 63 (No. 12, December 1986), pages 1579–1583, recommends tertiary amides of the formula

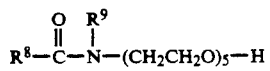

where $R^8$ and $R^9$ are each aliphatic alkyl radicals having a chainlength of from 7 to 10 carbon atoms, in particular 8 carbon atoms, for use as wetting agents for textiles. However, these compounds have pronounced application deficiencies, in particular excessive wetting times and excessive foaming, and the compounds tend to precipitate in the application baths.

U.S. Published Patent Application B 468 198 discloses tertiary amides of $C_8$–$C_{20}$-alkanoic and -alkenoic acids, for example of octanoic or of decanoic acid, which are substituted on the amide nitrogen by a polyoxy-alkylene radical and a $C_1$–$C_5$-alkyl radical for use as auxiliaries in the polymerization of chloroprene.

GB-A-2 169 916 relates to a detergent formulation containing as a surface-active component a tertiary amide of a $C_9$–$C_{21}$-alkanoic acid, in particular of a $C_{12}$–$C_{16}$-fatty acid, substituted at the amide nitrogen by a polyoxyethylene radical and an alkyl radical having up to 3 carbon atoms.

It is an object of the present invention to make available wetting agents for use in the textile industry that are free of the prior art deficiencies described.

We have found that this object is achieved by the use of tertiary amides of the general formula I

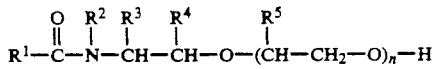

where
$R^1$ is straight-chain or branched $C_5$–$C_{17}$-alkyl or -alkenyl,
$R^2$ is straight-chain or branched $C_3$–$C_6$-alkyl,
$R^3$, $R^4$ and $R^5$ are each independently of the others hydrogen, methyl or ethyl, and
n is from 3 to 15,
as low-foam wetting agents in the manufacture and finishing of textiles.

$R^1$ is preferably straight-chain or branched $C_6$–$C_{15}$-alkyl, in particular $C_7$–$C_{13}$-alkyl. Examples of $R^1$ are n-pentyl, n-hexyl, n-heptyl, 3-heptyl (derived from 2-ethylhexanoic acid), n-octyl, 2,4,4-trimethylpentyl (derived from the main component of isononanoic acid), n-nonyl, n-decyl, n-undecyl, n-dodecyl, n-tridecyl, n-tetradecyl, n-pentadecyl, n-hexadecyl, n-heptadecyl (derived from stearic acid) and cis-8-heptadecenyl (derived from oleic acid). Particularly effective wetting agents are obtained when $R^1$ is derived from nonanoic acid and in particular from isononanoic acid.

$R^2$ is preferably straight-chain or branched $C_4$–$C_6$-alkyl, in particular straight-chain alkyl such as n-butyl, n-pentyl or n-hexyl. But $R^2$ can also be n-propyl, isopropyl, sec-butyl, isobutyl, tert-butyl, sec-pentyl, isopentyl, tert-pentyl, neopentyl, 2-, 3- or 4-methylpentyl, or 2,3- or 3,3-dimethylbutyl.

$R^3$, $R^4$ and $R^5$ are each preferably hydrogen.

n is preferably from 5 to 10.

The tertiary amides I are preparable by methods known in principle. One advantageous method is to react amides of the general formula II

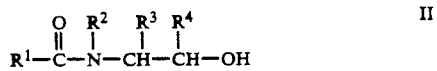

where each of $R^1$ to $R^4$ is as defined above, in a conventional manner with a $C_2$–$C_4$-alkylene oxide such as propylene oxide, butylene oxide or in particular ethylene oxide. This reaction is in general carried out under superatmospheric pressure at about 2–15 bar, in particular 4–10 bar, and at about 80°–170° C., in particular 100°–150° C. The alkoxylation can be catalyzed with any substance customary for this purpose, but potassium tert-butoxide is particularly useful. The alkoxylation products are worked up in a conventional manner; unconverted alkylene oxide is normally removed under reduced pressure.

The amides II are readily obtainable for example from the corresponding carboxylic acids of the general formula III

and the corresponding secondary amines of the general formula IV

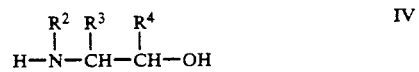

by reaction at elevated temperature.

The tertiary amides I of the invention are highly useful as low-foam wetting agents in the manufacture and finishing of textiles, in particular in dyeing and the preparatory and pretreatment stages therefor. Suitable textile materials here are in particular cotton and cotton blend fabrics.

As well as being low-foaming, the compounds I are advantageous in having short wetting times. Also, they do not tend to precipitate in the application baths.

Some of the tertiary amides I are novel compounds. Therefore the invention further provides tertiary amides of the general formula Ia

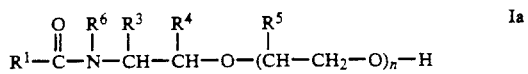

where
$R^1$ is a straight-chain or branched $C_5$–$C_{17}$-alkyl or -alkenyl radical, $R^3$ to $R^5$ are independently of one another hydrogen, methyl or ethyl, $R^6$ is n-butyl, n-pentyl or a straight-chain or branched $C_6$-alkyl radical, and n is from 3 to 15.

The present invention further provides tertiary amides of the general formula Ib

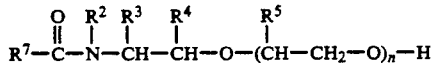

where $R^2$ is a straight-chain or branched $C_3$–$C_6$-alkyl radical, $R^3$ to $R^5$ are independently of one another hydrogen, methyl or ethyl, $R^7$ is the radical of nonanoic or isononanoic acid, and n is from 3 to 5.

PREPARATION EXAMPLES

Example 1

To 158.2 g (1.0 mol) of nonanoic (pelargonic) acid were added at ambient temperature 175.8 g (1.5 mol) of N-butylethanolamine under a protective gas atmosphere. The mixture was then stirred at 140° C. for 2 h, at 150° C. for 6 h and at 160° C. for 8 h. To remove the excess N-butylethanolamine, the pressure was reduced to 0.1 mbar for 2 h. This produced 250 g (corresponding to a yield of 91%) of N-butyl-N-(2-hydroxyethyl)-nonanamide. 128.7 g (0.5 mol) of this amide were admixed in an autoclave with 1.3 g of potassium tert-butoxide and reacted a little at a time at from 110° to 120° C. with 165 g (3.75 mol) of ethylene oxide at from 5 to 10 bar. After the ethoxylation had ended, small amounts of unconverted ethylene oxide were removed at 80° C./1 mbar in the course of 1 h, leaving 290 g of the 7.5 EO adduct.

Example 2

Example 1 was repeated with isononanoic acid and N-butylethanolamine in the first stage and 10 mol of ethylene oxide per mole of intermediate in the second stage to prepare the 10 EO adduct with N-butyl-N-(2-hydroxyethyl)isononanamide.

Example 3

Example 1 was repeated with isononanoic acid and N-hexylethanolamine in the first stage and 8 mol of ethylene oxide per mole of intermediate in the second stage to prepare the 8 EO adduct with N-hexyl-N-(2-hydroxyethyl)isononanamide.

Example 4

Example 1 was repeated with isononanoic acid and N-hexylisopropanolamine in the first stage and 9 mol of ethylene oxide per mole of intermediate in the second stage to prepare the 9 EO adduct with N-hexyl-N-(2-hydroxypropyl)isononanamide.

Comparative Example A

Example 1 was repeated with nonanoic acid and N-(2-ethylhexyl)ethanolamine in the first stage and 10 mol of ethylene oxide per mole of intermediate in the second stage to prepare the 10 EO adduct with N-(2-ethylhexyl)-N-(2-hydroxyethyl)nonanamide.

Comparative Example B

Example 1 was repeated with isononanoic acid and N-(2-ethylhexyl)ethanolamine in the first stage and 10 mol of ethylene oxide per mole of intermediate in the second stage to prepare the 10 EO adduct with N-(2-ethylhexyl-N-(2-hydroxyethyl)isononanamide.

Application Examples

The wetting power was determined by the dip wetting method of DIN 53901. In this test a standardized piece of cotton fabric is introduced with a clamp into an aqueous solution of the surfactant. As a result of wetting, liquid penetrates into the fabric, displacing the air and compensating the buoyancy. The fabric then sinks to the bottom. The quantity measured is the time between the fabric being introduced into the solution and the onset of sinking.

Table 1 reports the wetting times of the neutral 0.2% strength by weight solutions of the in-test substances.

TABLE 1

| Substance of Ex. No. | Wetting time [sec] | |
|---|---|---|
| | at 25° C. | at 70° C. |
| according to the invention: | | |
| 1 | 48 | — |
| 2 | 29 | 40 |
| 3 | 22 | 22 |
| 4 | 15 | 34 |
| for comparison: | | |
| A | 11 | precipitation |
| B | 12 | precipitation |

The degree of foaming was determined by the modified whipped foam method of DIN 53 902. In this test an aqueous solution of the in-test surfactant is introduced into a graduated cylinder and the solution is agitated with a perforated disc attached to a rod to produce foam. The quantity measured is the foam volume at 30, 60 and 120 seconds.

Table 2 shows the degree of foaming of the neutral 0.2% strength by weight solutions of the in-test substances.

TABLE 2

| Substance of Ex. No. | Foam volume [ml] | |
|---|---|---|
| | at 25° C. | at 70° C. |
| according to the invention: | | |
| 1 | 10/10/10 | 0/0/0 |
| 2 | 10/10/0 | 10/10/10 |
| 3 | 50/40/30 | 0/0/0 |
| 4 | 120/70/50 | 10/0/0 |
| for comparison: | | |
| A | 460/400/360 | 300/210/80 |
| B | 90/40/20 | 20/10/10 |

We claim:

1. A process for manufacturing and finishing textiles, which comprises using tertiary amides of the general formula

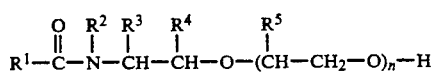

where $R^1$ is straight-chain or branched $C_5$–$C_{17}$-alkyl or -alkenyl, $R^2$ is straight-chain or branched $C_3$–$C_6$-alkyl, $R^3$, $R^4$ and $R^5$ are each independently of the others hydrogen, methyl or ethyl, and n is from 3 to 15, as low-foam wetting agents.

2. A process as claimed in claim 1, wherein $R^1$ is a straight-chain or branched $C_6$–$C_{15}$-alkyl.

3. A process as claimed in claim 1, wherein $R^2$ is a straight-chain or branched $C_4$–$C_6$-alkyl radical.

4. A process as claimed in claim 1, wherein $R^3$, $R^4$ and $R^5$ are each hydrogen.

5. A process as claimed in claim 1, wherein n is from 5 to 10.

6. Tertiary amides of the general formula Ia

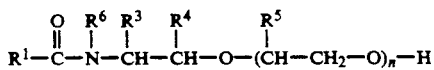

where $R^1$ is straight-chain or branched $C_5$–$C_{17}$-alkyl or -alkenyl, $R^3$ to $R^5$ are independently of one another hydrogen, methyl or ethyl, $R^6$ is n-butyl, n-pentyl or straight-chain or branched $C_6$-alkyl, and n is from 3 to 5.

7. Tertiary amides of the general formula Ib

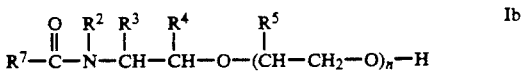

where $R^2$ is straight-chain or branched $C_3$–$C_6$-alkyl, $R^3$ to $R^5$ are independently of one another hydrogen, methyl or ethyl, $R^7$ is the radical of nonanoic or isononanoic acid, and n is from 3 to 5.

* * * * *